(12) United States Patent
Griswold et al.

(10) Patent No.: US 8,717,020 B2
(45) Date of Patent: May 6, 2014

(54) NON-CARTESIAN CAIPIRINHA

(76) Inventors: Mark A. Griswold, Shaker Heights, OH (US); Stephen R. Yutzy, University Heights, OH (US); Nicole E. Seiberlich, Shaker Heights, OH (US)

(*) Notice: Subject to any disclaimer, the term of this patent is extended or adjusted under 35 U.S.C. 154(b) by 1231 days.

(21) Appl. No.: 12/603,758

(22) Filed: Oct. 22, 2009

(65) Prior Publication Data

US 2011/0096092 A1    Apr. 28, 2011

(51) Int. Cl.
*G09G 5/00*     (2006.01)
*G01R 33/44*    (2006.01)

(52) U.S. Cl.
USPC .......................... 324/309; 324/307; 345/630

(58) Field of Classification Search
USPC ........... 324/307, 309; 600/410; 382/195, 275; 345/630
See application file for complete search history.

(56) References Cited

U.S. PATENT DOCUMENTS

| 2004/0222794 | A1* | 11/2004 | Griswold et al. | 324/309 |
| 2010/0142823 | A1* | 6/2010 | Wang et al. | 382/195 |
| 2011/0254548 | A1* | 10/2011 | Setsompop et al. | 324/309 |
| 2013/0076352 | A1* | 3/2013 | Block et al. | 324/307 |

OTHER PUBLICATIONS

Breuer et al.; "Zigzag sampling for improved parallel imaging"; Jul. 29, 2008; Magnetic Resonance in Medicine, vol. 60, Issue 2, pp. 474-478.*
Pruessmann et al.; "Advances in sensitivity encoding with arbitrary k-space trajectories"; Oct. 2, 2001; Magnetic Resonance in Medicine, vol. 46, Issue 4, pp. 638-651.*
Wu et al.; "Improved matrix inversion in image plane parallel MRI"; Mar. 9, 2009; Magnetic Resonance Imaging, vol. 27, Issue 7, pp. 942-953.*

* cited by examiner

*Primary Examiner* — Melissa Koval
*Assistant Examiner* — Rishi Patel

(57) ABSTRACT

Example systems, methods, and apparatus concern non-Cartesian CAIPIRINHA (Controlled Aliasing In Parallel Imaging Results IN Higher Acceleration). One example parallel magnetic resonance imaging (pMRI) apparatus includes a radio frequency (RF) manipulation logic configured to control the pMRI apparatus to perform a non-Cartesian CAIPIRINHA acquisition process in which under-sampled data is acquired using a non-Cartesian (e.g., radial) pattern. The apparatus also includes a reconstruction logic configured to reconstruct the under-sampled data as a function of phase shift applied by the non-Cartesian CAIPIRINHA acquisition process and coil sensitivities acquired during the non-Cartesian CAIPIRINHA acquisition process.

17 Claims, 8 Drawing Sheets

NON-CARTESIAN CAIPIRINHA

COPYRIGHT NOTICE

A portion of the disclosure of this patent document contains material that is subject to copyright protection. The copyright owner has no objection to the facsimile reproduction of the patent document or the patent disclosure as it appears in the Patent and Trademark Office patent file or records, but otherwise reserves all copyright rights whatsoever.

BACKGROUND

Magnetic resonance imaging (MRI) involves selectively exciting spins in pre-determined controllable ways in an object to be imaged. Transmission elements, magnets, gradient coils, and other elements are controlled to produce the selective excitation through a combination of spatially varying magnetic fields and controlled application of radio frequency (RF) energy at a specific frequency determined as a function of the Larmor frequency of spins to be excited. Spatial localization in MRI may be accomplished using, for example, spatially varying gradients to encode the frequency and phase of a signal. The selective excitation facilitates distinguishing signal from one volume (e.g., voxel, slice, band) in an object being imaged from signal from another volume in the object. Distinctions may be made based on frequency, phase, and other attributes.

Receive elements (e.g., coils) receive signals produced by the selectively excited spins. The total signal received at an individual receive element may have been produced by spins in more than one volume. Computers therefore process the received signals to separate signal contributions from different volumes and to produce an image.

Parallel MRI (pMRI) facilitates acquiring MR images more quickly than non-pMRI. pMRI techniques may selectively excite two or more volumes (e.g., slices) at the same time and may acquire signal from the two or more volumes at the same time. Some pMRI techniques rely, at least partially, on a spatially distinct arrangement of signal receiver coils. Spatial variation in individual coil elements can replace spatial encoding that is conventionally achieved using spatially-varying magnetic fields. At least one pMRI technique (CAIPIRINHA) involves applying a unique phase pattern to each simultaneously acquired volume (e.g., slice). CAIPIRINHA is described in Breuer et al., Magn. Reson. Mod 2005; 53(3): 684-691. CAIPIRINHA is also described in U.S. Pat. No. 7,002,344, which is titled "Data acquisition method for accelerated magnetic resonance imaging in framework of the parallel acquisition of MRT data". CAIPIRINHA stands for Controlled Aliasing In Parallel Imaging Results IN Higher Acceleration.

In some parallel imaging techniques, aliasing artifacts resulting from an under-sampled acquisition are removed by means of a specialized image reconstruction algorithm. In CAIPIRINHA, the appearance of aliasing artifacts are modified during acquisition to improve the subsequent parallel image reconstruction procedure. CAIPIRINHA is a parallel multi-slice technique that is more efficient than other multi-slice parallel imaging concepts that use only a pure post-processing approach. In CAIPIRINHA, multiple slices of arbitrary thickness and distance are excited simultaneously with the use of multi-band RE pulses similar to Hadamard pulses. These data are then under-sampled, yielding superimposed slices that appear shifted with respect to each other. The shift of the aliased slices is controlled by modulating the phase of the individual slices in the multi-band excitation pulse from echo to echo. Slices that have essentially the same coil sensitivity profiles can be separated with this technique.

Conventionally, MRI and pMRI may have used Cartesian signal acquisition patterns. Some MRI has used other signal acquisition patterns including, spiral, radial, and so on. However, radial acquisition may not have been considered for use with phase shifting parallel imaging like CAIPIRINHA since there is no way to shift one slice or volume with respect to another using only phase modulation of the RF pulse. Thus prior CAIPIRINHA methods are not compatible with a radial trajectory.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
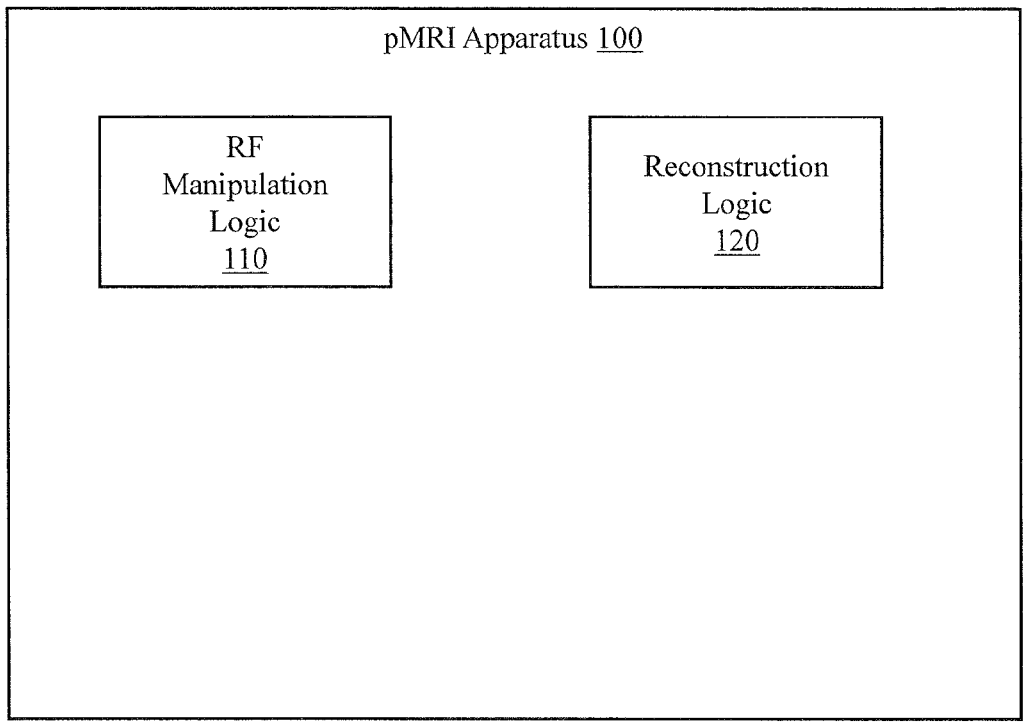
FIG. 1 illustrates one embodiment of a pMRI apparatus configured to perform a non-Cartesian CAIPIRINHA.

Example systems and methods concern non-Cartesian (e.g., radial) CAIPIRINHA. Example systems and methods combine RF phase manipulation with non-Cartesian acquisition schemes in a parallel imaging reconstruction. Example systems and methods achieve higher acceleration factors with higher image quality (as measured by SNR and g-factor) when compared to Cartesian acquisition schemes.

Example pMRI systems and methods combine the application of different phase patterns to simultaneously acquired volumes with a non-Cartesian (e.g., radial) sampling scheme with a sophisticated parallel reconstruction technique to produce high quality MR images at previously unattainable acceleration factors. The parallel reconstruction technique can be, for example, a parallel and/or iterative conjugate gradient (CG) reconstruction that accounts for applied phase shift and coil sensitivities.

The quality of an under-sampled MR image can be measured by, for example, signal to noise ratio (SNR), g-factor, and artifact power (AP). R is the acceleration factor and describes the degree of under-sampling in a data acquisition. SNR is proportional to the square root of the excited volume. pMRI techniques experience SNR decrease relative to fully sampled equivalents. The decrease can be measured according to:

$$SNR_{ppl} = \frac{SNR_{full}}{g\sqrt{R}}$$

AP may be measured according to:

$$AP = \frac{\sum_{i=1}^{voxels}(|\rho_i| - |\rho_{ref,i}|)^2}{\sum_{i=1}^{voxels}|\rho_{ref,i}|^2}$$

Conventionally, CAIPIRINHA has demonstrated unacceptable increases in AP at higher R values. For example, while at R=2 the increase in AP over a fully sampled data set may only increase by a negligible amount, at R=6 the AP has historically increased by up to 400% and at R=10 the AP has historically increased by up to 1000%, making an image unusable.

Example pMRI systems and methods exhibit improved performance at higher R values as compared to conventional systems. For example, at R=6 the AP may increase by only 1% and at R=10 the AP may increase by less than 40%, yielding a useable image created from a significantly under-sampled data set that can be acquired in a shorter period of time than a fully sampled data set. SNR loss due to increasing acceleration factors (R) can be accounted for by volumetric excitation techniques (e.g., multiband excitation).

G is the geometry factor and is a measure that describes how well pixels that are aliased due to a specific under-sampling pattern can be separated by characteristics of a receiver array. G is a function of the number of receive coils, the spatial sensitivity variation of receive coils, noise correlations, and the form of k-space accelerated sampling pattern. Example pMRI systems and methods can reduce g-factor losses by reducing the amount of aliased energy produced.

Example pMRI systems and methods that apply different phase patterns to simultaneously acquired volumes rely on three foundations. First, in a radial acquisition, line-dependant phase yields destructive interference at the center of k-space. This destructive interference destroys coherent signal from a volume (e.g., slice). Second, reconstruction of simultaneously acquired radial data with one volume phase cycled produces an image of one volume plus incoherent noise from the second volume. Since the phase cycling pattern is known, the phase can be undone in post-processing to produce an image of the second volume plus incoherent noise from the first volume. Third, incoherent noise from a simultaneously acquired volume can be reduced by a customized parallel imaging reconstruction technique (e.g. iterative CG). The customized technique will use coil sensitivity maps for both volumes while processing signal from simultaneous sampling of multiple volumes.

Example non-Cartesian CAIPIRINHA pMRI techniques reduce g-factor losses by uniquely phase cycling individual volumes (e.g., bands, slices) in a multi-volume excitation. This phase cycling reduces the number of locations where multiple slices are contributing signal to an under-sampled image, thereby reducing aliasing energy that would need to be accounted for in pMRI reconstruction. Coil sensitivity information is acquired for volumes that are to be simultaneously acquired.

To summarize, example non-Cartesian CAIPIRINHA pMRI techniques yield less aliasing energy, and intentionally use destructive interference that reduces signal from a slice into incoherent noise.

In one embodiment, a pMRI reconstruction method employs an iterative CG approach. The iterative CG approach relies on the fact that the pMRI technique controlled the phase cycling and therefore has information concerning phase accumulation that can be used during reconstruction. For example, multiplication of raw signal data by the complex conjugate phase can be used to restore signal levels in a phase cycled slice to yield a coherent reconstruction. In non-Cartesian CAIPIRINHA pMRI techniques, a slice estimate for one slice from a set of simultaneously acquired slices has signal from that one slice and from other slices in the set. The signal from the other slices in the set can be treated as incoherent noise but can also be used to retrieve the second slice. Since well known and distinct coil sensitivity patterns for members of the set of slices are known, the contribution of signal from other members of the set of slices can be accounted for and reduced for the one slice. Additionally, what is incoherent noise from one phase cycled point of view, is signal that can be reconstructed from another phase cycled point of view. Therefore multiple (e.g., two) slices can be recovered by reconstructing the raw data and the raw data modulated by the conjugate phase pattern.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable medium", as used herein, refers to a medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

"Signal", as used herein, includes but is not limited to, electrical signals, optical signals, analog signals, digital signals, data, computer instructions, processor instructions, messages, a bit, a bit stream, or other means that can be received, transmitted and/or detected.

FIG. 1 illustrates one embodiment of a pMRI apparatus 100 that is configured to perform a non-Cartesian CAIPIRINHA process. The non-Cartesian CAIPIRINHA process may be, for example, a radial CAIPIRINHA process. Apparatus 100 includes an RF manipulation logic 110. The RF manipulation logic is configured to control the pMRI apparatus 100 to perform a non-Cartesian CAIPIRINHA process in which under-sampled data is acquired from multiple slices that are excited with different phase patterns using a non-Cartesian pattern. The non-Cartesian pattern may be, for example, a radial pattern. One skilled in the art will appreciate that other non-Cartesian patterns may be employed.

Apparatus 100 also includes a reconstruction logic 120. Reconstruction logic 120 is configured to reconstruct under-sampled data that is acquired during the non-Cartesian CAIPIRINHA. The reconstruction depends, at least in part, on the phase shift applied by the non-Cartesian CAIPIRINHA process and on the coil sensitivities.

The pMRI apparatus illustrates improved performance over conventional pMRI apparatus that perform only Cartesian CAIPIRINHA processes. In one embodiment, at an acceleration factor of four, an artifact power associated with artifact signal in an image reconstructed from the under-sampled data by the reconstruction logic is less than two percent greater than a corresponding artifact power in a corresponding fully sampled reconstruction. In another embodiment, at an acceleration factor of ten, an artifact power associated with artifact signal in an image reconstructed from the under-sampled data by the reconstruction logic is less than forty percent greater than a corresponding artifact power in a corresponding fully sampled reconstruction. While improvements at R=4 and R=10 are described, one skilled in the art will appreciate that improvements can be achieved at other acceleration factors.

A non-Cartesian CAIPIRINHA process yields a first slice and a second slice. The first slice includes signal from the second slice and the second slice includes signal from the first slice. Therefore, the reconstruction logic 120 is configured to perform a first conjugate phase multiplication on the first slice to restore signal associated with the first slice in the first slice while causing signal from the second slice to become incoherent signal in the first slice. The reconstruction logic 120 is also configured to perform a second conjugate phase multiplication on the second slice to restore signal associated with the second slice in the second slice while causing signal from the first slice to become incoherent signal in the second slice. While two slices are described, one skilled in the art will appreciate that two or more slices may be excited, acquired, and reconstructed using example systems, methods, and apparatus described herein.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 2:
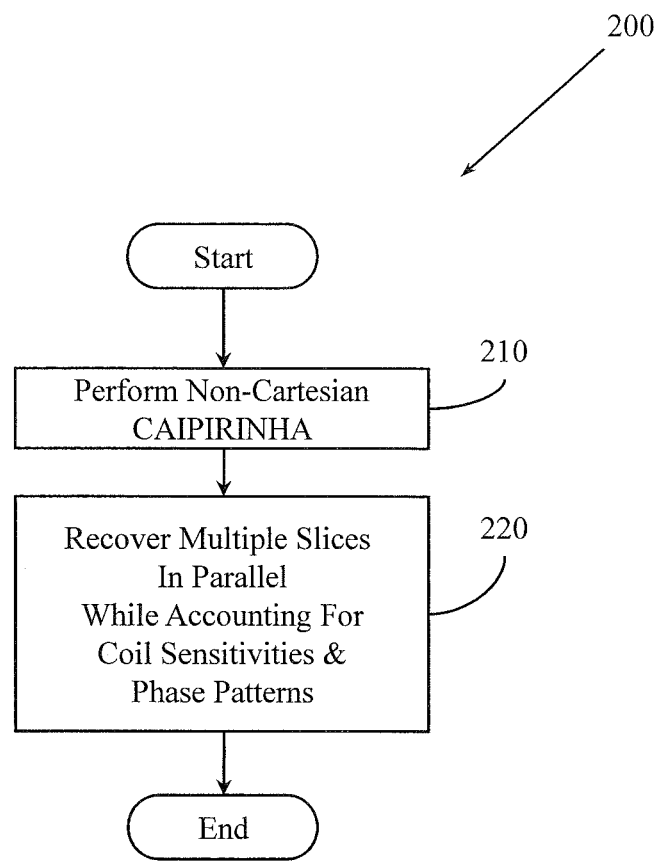
FIG. 2 illustrates one embodiment a method to control a pMRI apparatus to perform a non-Cartesian CAIPIRINHA.

FIG. 2 illustrates one embodiment of a method 200 to control a pMRI apparatus to perform a non-Cartesian CAIPIRINHA. Method 200 includes, at 210, controlling the pMRI apparatus to perform a CAIPIRINHA process that acquires under-sampled data from at least two slices. The under-sampled data is acquired using a non-Cartesian pattern. For example, a radial acquisition pattern can be employed.

Method 200 also includes, at 220, controlling the pMRI apparatus to recover, in parallel, the at least two slices. Recovering the at least two slices can involve several actions. In one embodiment, recovering the at least two slices can include controlling the pMRI apparatus to reconstruct raw under-sampled data received in coils in an array of receive coils in the pMRI apparatus. Once the raw under-sampled data has been reconstructed, recovering the at least two slices can also include, controlling the pMRI apparatus to reconstruct the raw under-sampled data as modulated by conjugate phase patterns applied to the at least two slices during the CAIPIRINHA process.

Like apparatus 100 (FIG. 1) achieves improved performance over conventional apparatus, so too does method 200 illustrate improved performance over conventional methods. In one example, at an acceleration factor of four, an AP associated with artifact signal in an image reconstructed from the under-sampled data is less than two percent greater than an AP in a corresponding fully sampled reconstruction. Additionally, at an acceleration factor of ten, an AP associated with artifact signal in an image reconstructed from the under-sampled data is less than forty percent greater than an AP in a corresponding fully sampled reconstruction.

Figure 3:
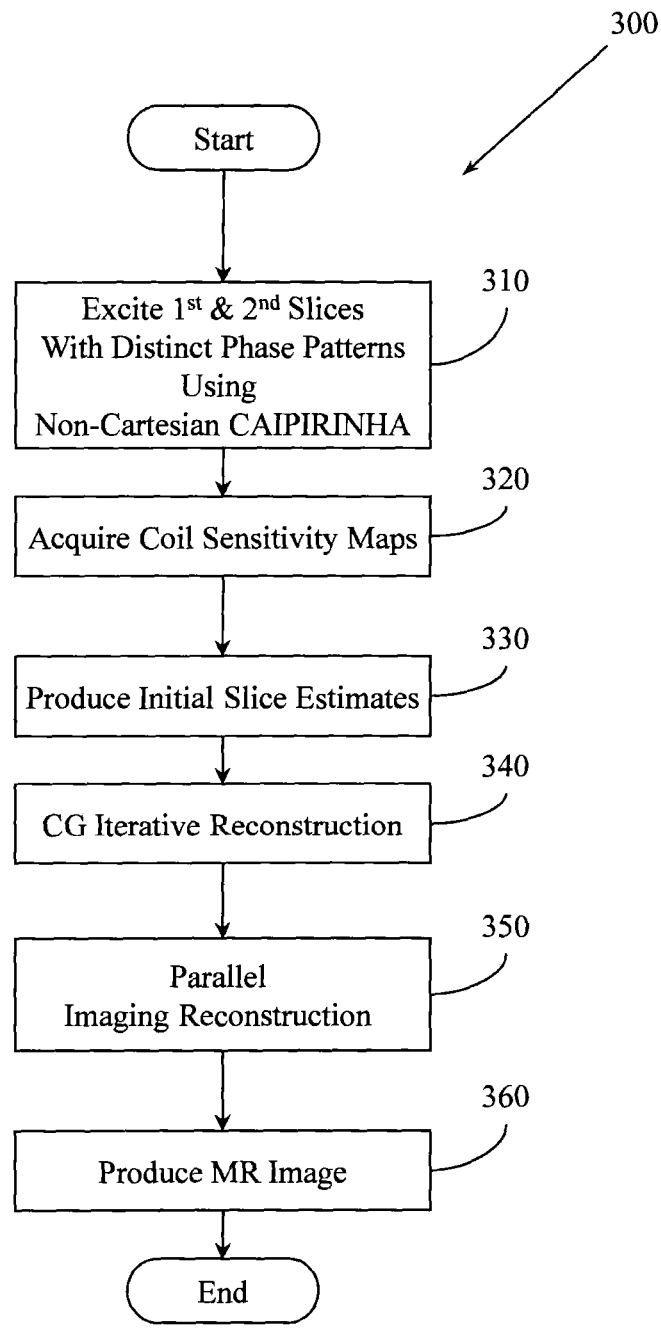
FIG. 3 illustrates one embodiment of a method to control a pMRI apparatus to perform a non-Cartesian (e.g., radial) CAIPIRINHA.

FIG. 3 illustrates one embodiment of a method 300 to control a pMRI apparatus to perform a non-Cartesian CAIPIRINHA. Method 300 includes, at 310, controlling a pMRI apparatus to excite a first slice with a first phase pattern and to excite a second different slice with a second different phase pattern. In one embodiment, the difference between the first phase pattern and the second phase pattern is based on a random number generator. In one embodiment, the difference between the first phase pattern and the second phase pattern is $\pi$ radians. While two phase patterns are described, one skilled in the art will appreciate that a greater number of slices and therefore a greater number of phase patterns may be excited. While a phase difference of $\pi$ radians is described, one skilled in the art will appreciate that other phase differences can be employed.

Method 300 also includes, at 320, controlling the pMRI apparatus to acquire a first coil sensitivity map for the first slice while the first slice is excited by the first phase pattern and to acquire a second coil sensitivity map for the second slice while the second slice is excited by the second phase pattern. While two slices and two coil sensitivity maps are described, one skilled in the art will appreciate that a greater number of slices and therefore a greater number of coil sensitivity maps may be acquired. One skilled in the art will also appreciate that other conventional means can also be used to acquire sensitivity maps.

Method 300 also includes, at 330, controlling the pMRI apparatus to acquire, in parallel, using an under-sampling radial acquisition technique, a first magnetic resonance (MR) signal from the first slice while the first slice is excited by the first phase pattern and a second MR signal from the second slice while the second slice is excited by the second phase pattern.

Method 300 also includes, at 340, controlling the pMRI apparatus to produce an initial first slice estimate for the first slice from the first MR signal and to produce an initial second slice estimate from the second MR signal. Recall that the initial first slice estimate will include signal from the first slice and signal from the second slice. Similarly, the initial second slice will include signal from the second slice and signal from the first slice. However, the information will have different image patterns due to the different phase patterns.

Method 300 also includes, at 350, controlling the pMRI apparatus to perform parallel imaging reconstruction to recover an improved first slice estimate and an improved second slice estimate. The parallel imaging reconstruction is based, at least in part, on the first coil sensitivity map and the second coil sensitivity map. The parallel imaging reconstruction is also based, at least in part, on the first phase pattern and the second phase pattern.

Method 300 also includes, at 360, producing an MR image from the improved first slice estimate and the improved second slice estimate. The MR image will demonstrate improved characteristics with respect to artifact power.

Figure 4:
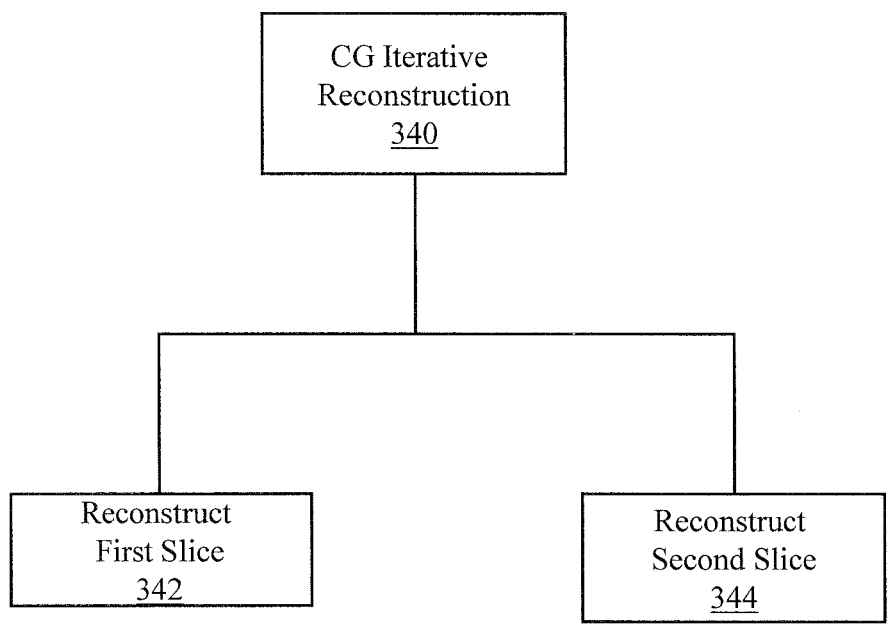
FIG. 4 illustrates additional detail for one embodiment of a method to control a pMRI apparatus to perform a non-Cartesian CAIPIRINHA.
Figure 8:
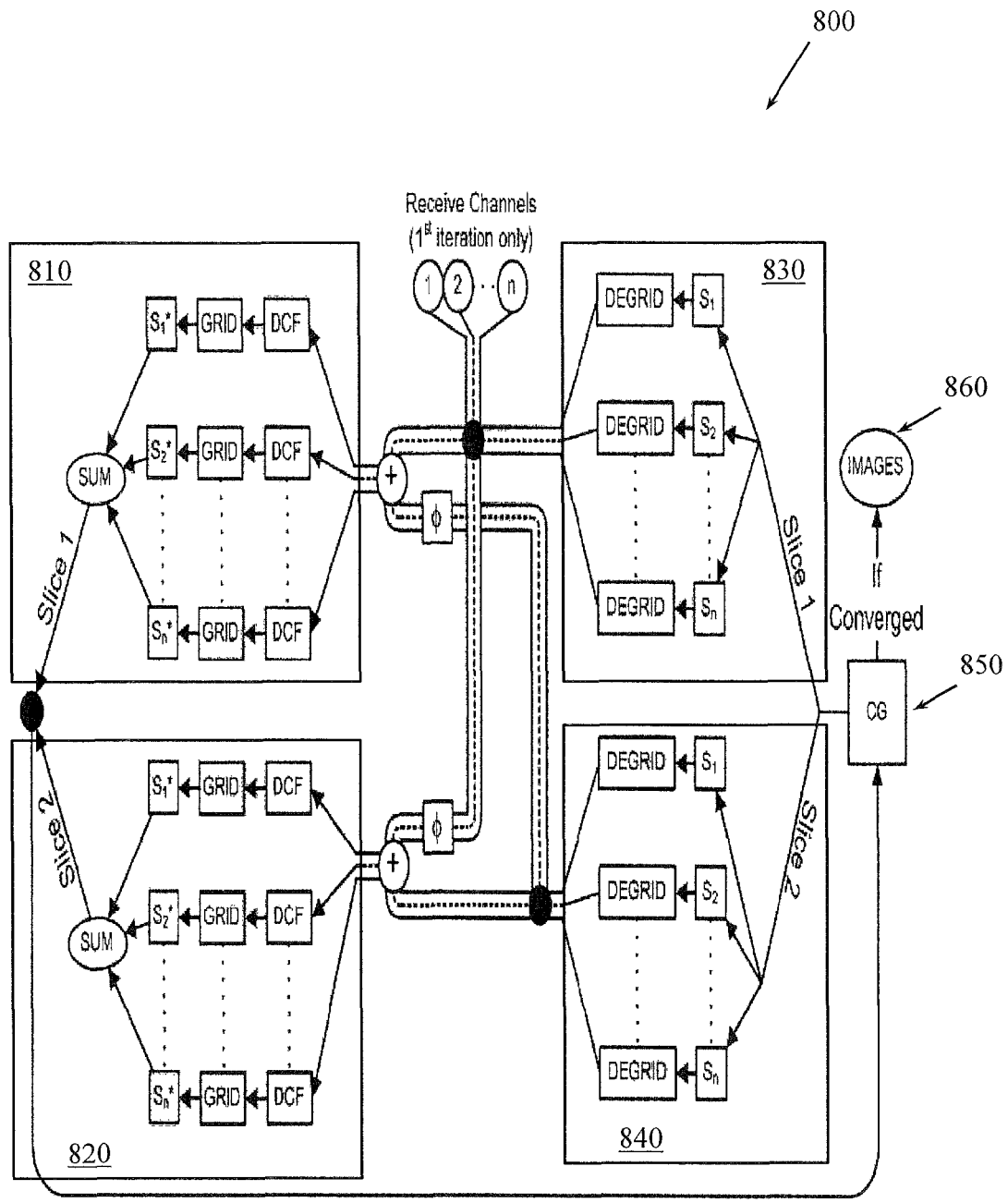
FIG. 8 illustrates one data flow associated with non-Cartesian CAIPIRINHA.

FIG. 4 illustrates additional detail for one embodiment of method 300. One skilled in the art will appreciate that both slices are reconstructed simultaneously based on the coil sensitivities and phase patterns for both slices. A data flow related to the additional detail described for method 300 is illustrated in FIG. 8. The first additional details concern the iterative CG reconstruction performed at 340. In one embodiment, the iterative CG can include performing a set of actions for each slice being recovered. Recall that the different slices will have been excited with different phase patterns and that different coil sensitivity maps will be available for the different slices. However, the different slices will be reconstructed in parallel and/or substantially in parallel using data concerning the coil sensitivities and phase patterns for the different slices. Therefore, the CG Iterative reconstruction 340 is illustrated including reconstructing a first slice at 342 and reconstructing, in parallel and/or substantially in parallel, a second slice at 344.

While FIG. 3 illustrates various actions occurring in serial, it is to be appreciated that various actions illustrated in FIG. 3 could occur substantially in parallel. By way of illustration, a first process could excite first and second slices, a second process could acquire coil-sensitivity maps, a third process could produce initial slice estimates, a fourth process could perform a parallel imaging reconstruction, and a fifth process could produce an MR image. While five processes are described, it is to be appreciated that a greater and/or lesser number of processes could be employed and that lightweight processes, regular processes, threads, and other approaches could be employed.

In one example, a method may be implemented as computer executable instructions. Thus, in one example, a computer-readable medium may store computer executable instructions that if executed by a machine (e.g., processor) cause the machine to perform method 300. While executable instructions associated with the method 300 are described as being stored on a computer-readable medium, it is to be appreciated that executable instructions associated with other example methods described herein may also be stored on a computer-readable medium.

Figure 5:
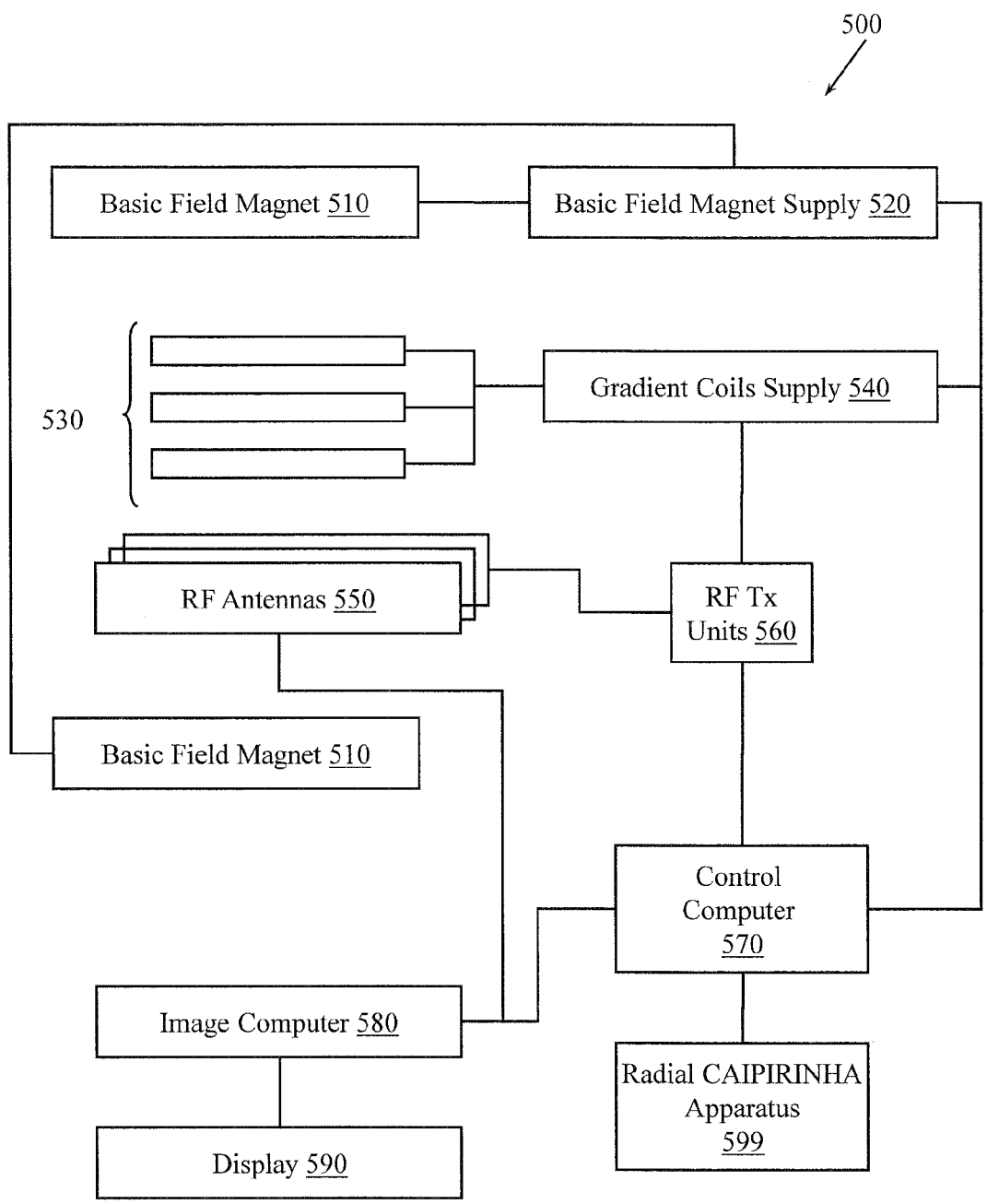
FIG. 5 illustrates an apparatus associated with non-Cartesian CAIPIRINHA.

FIG. 5 illustrates an example MRI apparatus 500 configured with a non-Cartesian CAIPIRINHA apparatus 599. The apparatus 599 may be configured with elements of example apparatus described herein and/or may perform example methods described herein. The apparatus 500 includes a basic field magnet(s) 510 and a basic field magnet supply 520. Ideally, the basic field magnets 510 would produce a uniform $B_0$ field. However, in practice, the $B_0$ field may not be uniform, and may vary over an object being imaged by the MRI apparatus 500. MRI apparatus 500 may include gradient coils 530 configured to emit gradient magnetic fields like $G_S$, $G_P$ and $G_R$. The gradient coils 530 may be controlled, at least in part, by a gradient coils supply 540. In some examples, the timing, strength, and orientation of the gradient magnetic fields may be controlled, and thus selectively adapted during an MRI procedure.

MRI apparatus 500 may include a set of RF antennas 550 that are configured to generate RF pulses and to receive resulting magnetic resonance signals from an object to which the RF pulses are directed. In some examples, how the pulses are generated and how the resulting MR signals are received may be controlled and thus may be selectively adapted during an MRI procedure. Separate RF transmission and reception coils can be employed. The RF antennas 550 may be controlled, at least in part, by a set of RF transmission units 560. An RF transmission unit 560 may provide a signal to an RF antenna 550.

The gradient coils supply 540 and the RF transmission units 560 may be controlled, at least in part, by a control computer 570. In one example, the control computer 570 may be programmed to control a pMRI device as described herein. The magnetic resonance signals received from the RF antennas 550 can be employed to generate an image and thus may be subject to a transformation process. The transformation can be performed by an image computer 580 or other similar processing device. The image data may then be shown on a display 590. While FIG. 5 illustrates an example MRI apparatus 500 that includes various components connected in various ways, it is to be appreciated that other MRI apparatus may include other components connected in other ways.

Figure 6:
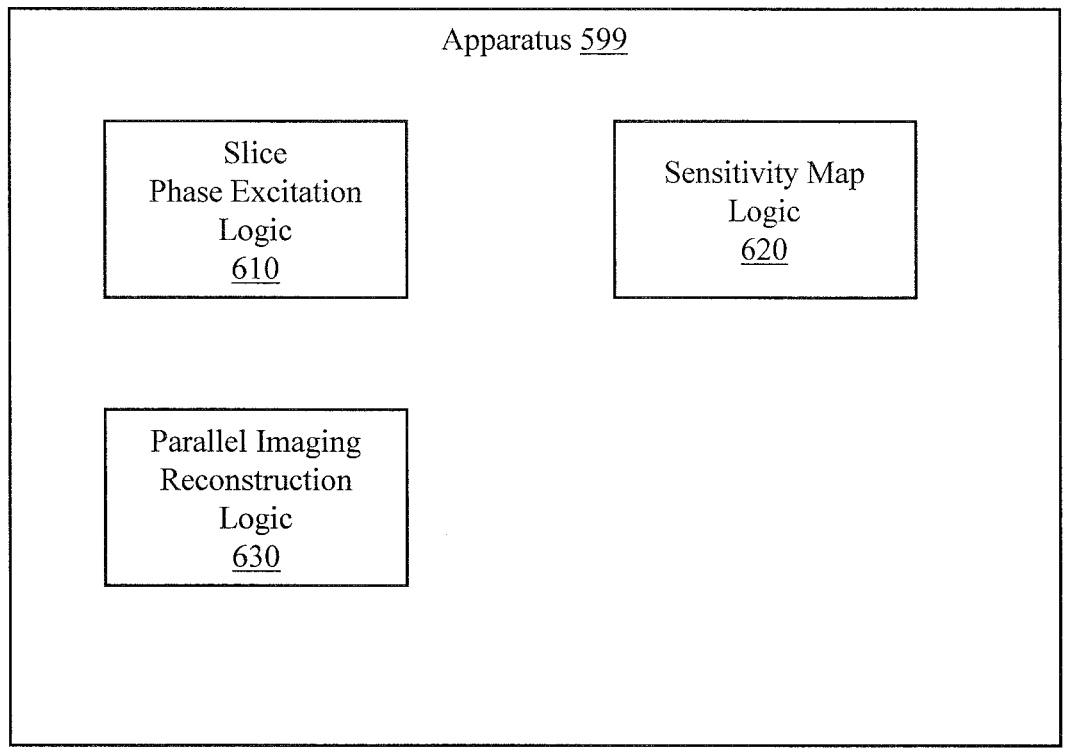
FIG. 6 illustrates an apparatus associated with non-Cartesian CAIPIRINHA.

FIG. 6 illustrates one embodiment of apparatus 599. The embodiment of apparatus 599 illustrated in FIG. 6 includes a slice phase excitation logic 610, a sensitivity map logic 620, and a parallel imaging logic 630. The slice phase excitation logic 610 is configured to control a pMRI apparatus to excite a first slice with a first phase pattern and to excite a second different slice with a second different phase pattern.

The sensitivity map logic 620 is configured to acquire a first coil sensitivity map for the first slice while the first slice and to acquire a second coil sensitivity map for the second slice.

The parallel imaging reconstruction logic 630 is configured to control the pMRI apparatus to produce an initial first slice estimate for the first slice from the first MR signal and to produce an initial second slice estimate from the second MR signal. The parallel imaging reconstruction logic 630 is also configured to control the pMRI apparatus to recover an improved first slice estimate and an improved second slice estimate. The parallel imaging reconstruction is based, at least in part, on the first coil sensitivity map and the second coil sensitivity map. The parallel imaging reconstruction is also based, at least in part, on the first phase pattern and the second phase pattern.

Figure 7:
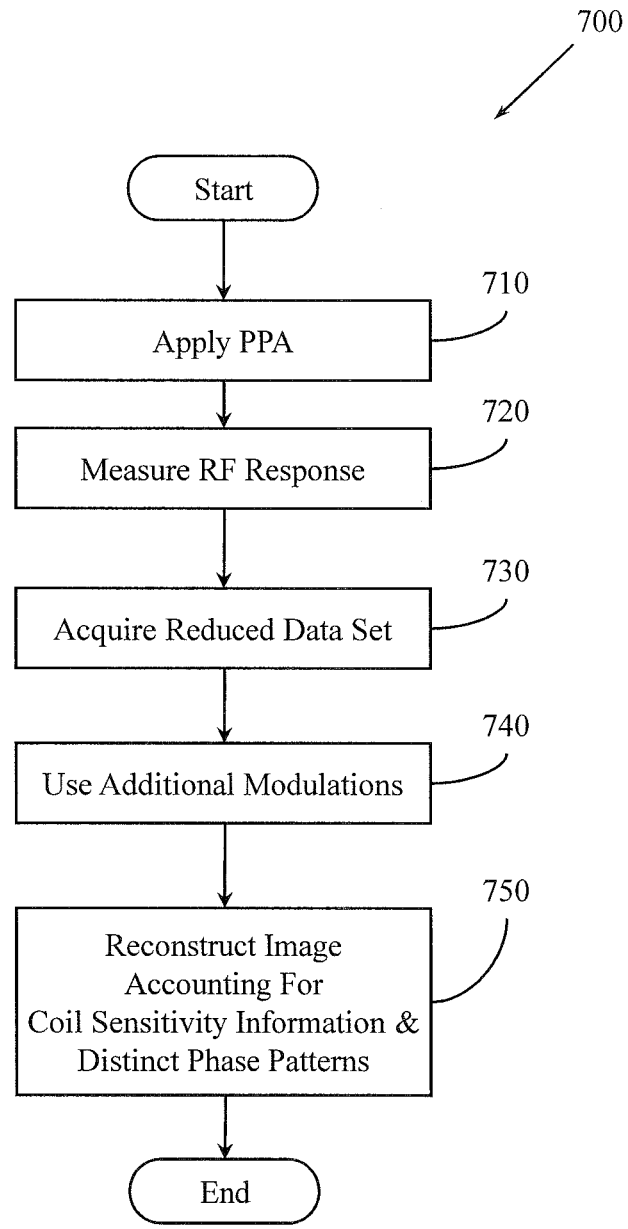
FIG. 7 illustrates a method associated with non-Cartesian CAIPIRINHA.

FIG. 7 illustrates a method 700 associated with non-Cartesian CAIPIRINHA. Method 700 is a method for magnetic resonance imaging (MRI) of a contiguous region of a subject. Method 700 includes, at 710, applying a non-Cartesian partially parallel acquisition (PPA) via modulation of spin magnetization using RF pulses as well as using spatial coding of the subject region with distinct phase patterns. The PPA also subsequently measures, in cycles, RF response signals showing excited spins.

Method 700 also includes, at 720, measuring the RF response signals acquired by a coil array. The coil array includes two or more RF receiver coils via which both coil sensitivity information and the radio-frequency response signals are acquired under the same phase pattern excitation conditions.

Method 700 also includes, at 730, acquiring, by each RF receiver coil, a reduced data set. Once again the reduced data set is acquired under the same phase pattern excitation conditions as the coil sensitivity information. The reduced data set will be reconstructed into an image. Method 700 also includes, at 740, utilizing additional modulations of spin magnetization. The additional modulations include modulations of RF pulses or additional modulation of gradients used for spatial coding of the subject regions.

Method 700 also includes, at 750, reconstructing, at least partially in parallel, at least two slices for which RF response signals showing excited spins were acquired. The reconstructing at 750 depends, at least in part, on the coil sensitivity information and the distinct phase patterns.

FIG. 8 illustrates one example data flow associated with non-Cartesian CAIPIRINHA. The data flow illustrates data being acquired for two slices. One skilled in the art will appreciate that data can be acquired for more than two slices. Raw data is initially acquired on receive channels. The initial raw data for the two slices is separated out and processed individually. Operations 810 are performed for the first slice and corresponding operations 820 are performed for the second slice. Operations 810 include multiplication by a density compensation function, re-sampling k-space data from the non-Cartesian acquisition to a Cartesian grid, and multiplication by the complex conjugate of the sensitivity of an appropriate coil. One skilled in the art will appreciate that FIG. 8 illustrates one example data flow and that other data flows can be employed.

Data from the first slice and the second are combined and then provided to a conjugate gradient reconstruction logic 850. If the logic 850 determines that data has converged, then images 860 are produced. Otherwise, operations 830 and 840 are performed for the first slice and the second slice respectively. Operations 830 include separating out individual slice information from the collective information, multiplication by complex sensitivity of an appropriate coil, and re-sampling image data back to the non-Cartesian k-space trajectory. The data processed by operations 830 and 840 is then selectively multiplied by a phase cycling pattern and returned to operations 810 and 820.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A parallel magnetic resonance imaging (pMRI) apparatus, comprising:
    a radio frequency (RF) manipulation logic configured to control the pMRI apparatus to perform a non-Cartesian CAIPIRINHA process in which under-sampled data is acquired using a non-Cartesian pattern; and
    a reconstruction logic configured to reconstruct the under-sampled data as a function of phase shift applied by the non-Cartesian CAIPIRINHA process and coil sensitivities acquired during the non-Cartesian CAIPIRINHA process,
    where, at an acceleration factor of ten, an artifact power associated with artifact signal in an image reconstructed from the under-sampled data by the reconstruction logic is less than forty percent greater than a corresponding artifact power in a corresponding fully sampled reconstruction.

2. The pMRI apparatus of claim 1,
    where the non-Cartesian CAIPIRINHA process yields a first slice and a second slice, where the first slice includes signal from the second slice, and where the second slice includes signal from the first slice, and
    where the reconstruction logic is configured to perform a first conjugate phase multiplication on the first slice to restore signal associated with the first slice in the first slice while causing signal from the second slice to become incoherent signal in the first slice, and where the reconstruction logic is configured to perform a second conjugate phase multiplication on the second slice to restore signal associated with the second slice in the second slice while causing signal from the first slice to become incoherent signal in the second slice.

3. A method for controlling a parallel magnetic resonance imaging (pMRI) apparatus, comprising:

controlling the pMRI apparatus to perform a CAIPIR-INHA process that acquires under-sampled data from at least two slices, the under-sampled data being acquired using a non-Cartesian pattern; and controlling the pMRI apparatus to recover, in parallel, the at least two slices, where performing the CAIPIRINHA process includes controlling the pMRI apparatus to excite a first excitation slice with a first phase pattern and to excite a second excitation slice with a second phase pattern, and where the difference between the first phase pattern and the second phase pattern is $\pi$ radians or is determined by the output of a random number generator.

4. The method of claim 3, where recovering, in parallel, the at least two slices, comprises:

controlling the pMRI apparatus to reconstruct raw under-sampled data received in coils in an array of receive coils in the pMRI apparatus; and controlling the pMRI apparatus to reconstruct the raw under-sampled data as modulated by conjugate phase patterns applied to the at least two slices during the CAIPIRINHA process.

5. The method of claim 3, where, at an acceleration factor of four, an artifact power associated with artifact signal in an image reconstructed from the under-sampled data is less than two percent greater than an artifact power in a corresponding fully sampled reconstruction.

6. The method of claim 3, where, at an acceleration factor of ten, an artifact power associated with artifact signal in an image reconstructed from the under-sampled data is less than forty percent greater than an artifact power in a corresponding fully sampled reconstruction.

7. A method, comprising:

controlling a parallel magnetic resonance imaging (pMRI) apparatus to excite a first slice with a first phase pattern and to excite a second different slice with a second different phase pattern, where the difference between the first phase pattern and the second phase pattern is $\pi$ radians or is determined by the output of a random number generator;

controlling the pMRI apparatus to acquire a first coil sensitivity map for the first slice and to acquire a second coil sensitivity map for the second slice;

controlling the pMRI apparatus to acquire, in parallel, using an under-sampling non-cartesian acquisition technique, a first magnetic resonance (MR) signal from the first slice while the first slice is excited by the first phase pattern and a second MR signal from the second slice while the second slice is excited by the second phase pattern;

controlling the pMRI apparatus to produce an initial first slice estimate for the first slice from the first MR signal and to produce an initial second slice estimate from the second MR signal;

controlling the pMRI apparatus to perform an iterative conjugate gradient (CG) reconstruction to recover an improved first slice estimate and an improved second slice estimate, where the iterative CG reconstruction continues until a termination condition occurs; and producing an MR image from the improved first slice estimate and the improved second slice estimate.

8. The method of claim 7, where the iterative CG reconstruction is based, at least in part, on the first coil sensitivity map and the second coil sensitivity map.

9. The method of claim 8, where the iterative CG reconstruction is based, at least in part, on the first phase pattern and the second phase pattern.

10. The method of claim 7, the iterative CG reconstruction comprising:

performing, for each slice:

multiplication, by a density compensation function, of data associated with each receive channel on which data for a slice is acquired;

re-sampling, to a Cartesian grid, k-space data sampled using the radial acquisition technique;

multiplication, by the complex conjugate of a coil, data acquired on the coil; and summing together data for each receive channel to form a collective data associated with a slice.

11. The method of claim 10, the iterative CG reconstruction comprising:

combining slices into a combined data set; and performing a conjugate gradient reconstruction on the combined data set.

12. The method of claim 11, the iterative CG reconstruction comprising:

upon determining that the CG reconstruction of the combined data set satisfied a convergence threshold, producing a magnetic resonance image from the combined data set.

13. The method of claim 12, the iterative CG reconstruction comprising:

upon determining that the CG reconstruction of the combined data set does not satisfy a convergence threshold:

dividing a slice out of the combine data set;

for a divided out slice:

multiplying the divided out slice by the complex conjugate sensitivity of a coil;

de-gridding the divided out slice back to the k-space trajectory used to acquire the divided out slice; and multiplying the divided out slice by the phase cycling pattern;

and performing another iteration of the reconstruction.

14. The method of claim 7, where the termination condition is one of, the relative change between the initial slice estimate and the updated slice estimate being less than an iteration threshold, the relative change between the initial slice estimate and the updated slice estimate increasing twice, and a maximum number of iterations occurring.

15. The method of claim 7, where, at an acceleration factor of four, an artifact power associated with artifact signal in the final volume estimate is less than two percent greater than an artifact power in a fully sampled reconstruction of the initial volume estimate.

16. The method of claim 7, where, at an acceleration factor of ten, an artifact power associated with artifact signal in the final volume estimate is less than forty percent greater than an artifact power in a fully sampled reconstruction of the initial volume estimate.

17. The method of claim 7, where the method is performed using an acceleration factor of 32 or more.

* * * * *

UNITED STATES PATENT AND TRADEMARK OFFICE
CERTIFICATE OF CORRECTION

Page 1 of 1

PATENT NO.         : 8,717,020 B2
APPLICATION NO.    : 12/603758
DATED              : May 6, 2014
INVENTOR(S)        : Griswold et al.

It is certified that error appears in the above-identified patent and that said Letters Patent is hereby corrected as shown below:

In the Specification:

In the Detailed Description:

In Column 9, line 61, delete "the second are" and insert --the second slice are--.

In the Claims:

In Column 11, line 54, delete "non-cartesian" and insert --non-Cartesian--.

Signed and Sealed this
Fourteenth Day of October, 2014

Michelle K. Lee
*Deputy Director of the United States Patent and Trademark Office*